United States Patent [19]

Giger

[11] Patent Number: 4,737,499
[45] Date of Patent: Apr. 12, 1988

[54] ERGOTALKALOIDS FOR TREATING SENILE DEMENTIA

[75] Inventor: Rudolf K. A. Giger, Riehen, Switzerland

[73] Assignee: Sandoz Ltd., Basel, Switzerland

[21] Appl. No.: 932,075

[22] Filed: Nov. 18, 1986

Related U.S. Application Data

[63] Continuation of Ser. No. 795,061, Nov. 5, 1985, abandoned, which is a continuation of Ser. No. 636,581, Aug. 1, 1984, abandoned, which is a continuation of Ser. No. 465,126, Feb. 9, 1983, abandoned.

[30] Foreign Application Priority Data

Feb. 12, 1982 [CH] Switzerland ............................ 893/82
Nov. 29, 1982 [CH] Switzerland .......................... 6924/82

[51] Int. Cl.$^4$ .................... A61K 31/48; C07D 519/02
[52] U.S. Cl. ...................................... 514/250; 544/346
[58] Field of Search ......................... 544/346; 514/250

[56] References Cited

U.S. PATENT DOCUMENTS

| 4,000,139 | 12/1976 | Stutz et al. | 544/346 |
| 4,091,099 | 5/1978 | Fehr et al. | 544/346 |
| 4,138,565 | 2/1979 | Ehrhardt et al. | 544/346 |

FOREIGN PATENT DOCUMENTS

| 141387 | 5/1985 | European Pat. Off. | 546/68 |
| 2700234 | 7/1977 | Fed. Rep. of Germany | 544/346 |
| 505102 | 5/1971 | Switzerland | 544/346 |
| 550801 | 6/1974 | Switzerland | 544/346 |

*Primary Examiner*—Donald G. Daus
*Assistant Examiner*—Cecilia Shen
*Attorney, Agent, or Firm*—Gerald D. Sharkin; Robert S. Honor; Thomas O. McGovern

[57] ABSTRACT

An ergot 5'S-(2R-butyl) peptide alkaloid and its acid addition salts is a useful pharmaceutical for use as a prolactin secretion inhibitor, for increasing vigilance or for the treatment of senile dementia, hypertension, or stroke.

25 Claims, No Drawings

ERGOTALKALOIDS FOR TREATING SENILE DEMENTIA

This is a continuation of application Ser. No. 795,061, filed Nov. 5, 1985, now abandoned, which in turn is a continuation of application Ser. No. 636,581, filed Aug. 1, 1984, now abandoned, which in turn is a continuation of application Ser. No. 465,126, filed Feb. 9, 1983, now abandoned.

This invention relates to ergot peptide alkaloids.

The present invention provides ergot 5'S-(2R-butyl) peptide alkaloids, hereinafter referred to as compounds of the invention, and their acid addition salts.

The ergot 5'S-(2R-butyl) compounds of the invention are hitherto totally unknown epimers of ergot peptide alkaloids, these latter alkaloids being preparable by chemical synthesis or, in some cases, also being found in nature or preparable by e.g. fermentation. They may be substituted. Furthermore, they may exist in the form of isomers, e.g. as the 8R or 8S isomers.

The chemistry of ergot peptide alkaloids has been recently reviewed in B. Berde and H. O. Schild "Ergot alkaloids and related compounds", 1978, Springer Verlag, Berlin in Chapter II, p. 29 to 85 by J. Rutschmann and P. Stadler. It is accepted that the known 5'S-(2-butyl) derivatives, e.g. β-ergocryptine, have the S configuration in the sec-butyl side chain (see p. 37 of the above mentioned B. Berde and H. O. Schild publication and also p. 2468 of Dictionary of Organic Compounds, 5th edition, Volume 3 Chapman and Hall, New York, 1982). The 2-butyl carbon atom having the S configuration is known under Chemical Abstracts nomenclature used in the 8th collective index as the 13' carbon atom.

In particular the present invention provides a compound of formula I

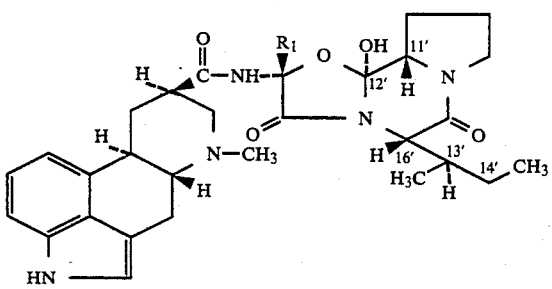

wherein $R_1$ is methyl, ethyl or isopropyl, and its acid addition salts.

The present invention in another aspect provides a process for the preparation of an ergot 5'S-(2R-butyl) peptide alkaloid or an acid addition salt thereof which includes the step of condensing an acid addition salt of a corresponding 5'S-(2R-butyl)aminocyclol or a precursor thereof with a reactive acid derivative of a corresponding lysergic acid derivative or a precursor thereof, and recovering the resultant above mentioned compound as such or as an acid addition salt thereof.

"Aminocyclol" covers typical tripeptides having a hydroxy group used in the synthesis of ergot peptide alkaloids. For example, they are cyclic tripeptides having an amino group in the 2' position and a hydroxy group in the 12' position.

A compound of formula I may be produced by a process which includes the step of condensing an acid addition salt of a compound of formula II

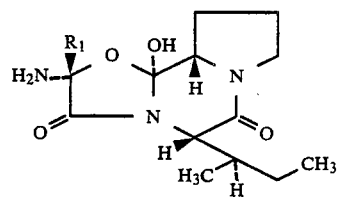

wherein $R_1$ is as defined above,
or a precursor thereof,
with a reactive acid derivative of a compound of formula III

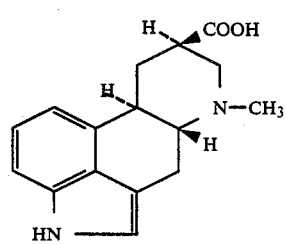

or a precursor thereof,
and recovering the resultant compound of formula I as such or as an acid addition salt thereof.

The condensation process of the invention may be effected in conventional manner for the production of analogous ergot peptide alkaloids.

An acid addition salt of the aminocyclol is for example the hydrochloride. A reactive acid derivative of the corresponding lysergic acid derivative is for example the acid chloride, or the mixed anhydride with sulfuric acid or trifluoroacetic acid. Alternatively the derivative may be the addition product produced from the corresponding lysergic acid with (i) dimethylformamide or acetamide and (ii) thionyl chloride, phosgene or oxalyl chloride. Preferably the reaction is effected in the presence of triethylamine or pyridine. Suitable solvents are for example chloroform, methylene chloride, dimethylformamide or acetonitrile. The reaction temperature may be for example from about $-30°$ C. to $+20°$ C.

As indicated above a precursor of the lysergic acid derivative or aminocyclol may be used e.g. a compound which may be converted into these compounds in conventional manner and subsequent to the condensation the resultant product may be converted into a compound of the invention or an acid addition salt thereof. Thus for example the lysergic acid derivative and/or aminocyclol may be in temporarily protected form.

The compounds of the invention may be converted into acid addition salts thereof in conventional manner and vice versa. A suitable acid addition salt is the hydrochloride or methanesulphonate.

The starting materials are known or may be produced in conventional manner from known compounds, e.g. as described below in respect of compounds of formula II which may be produced for example from compounds of formula IV

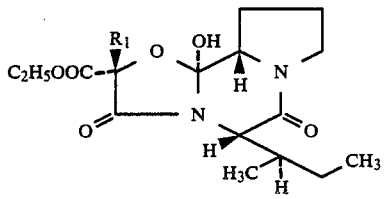

IV in conventional manner, e.g. via the hydrazide and benzyl ester as described in the examples.

The compound of formula IV may be produced by reacting a compound of formula V

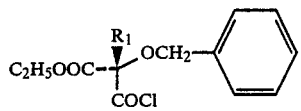

V with a compound of formula VI

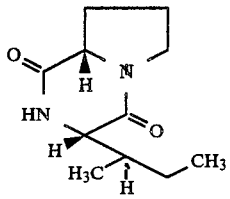

VI and hydrogenating the resultant tripeptide benzyl ether, e.g. as described in the examples.

The compound of formula VI may be produced e.g. as described in the following flow-sheet from optically active compounds:

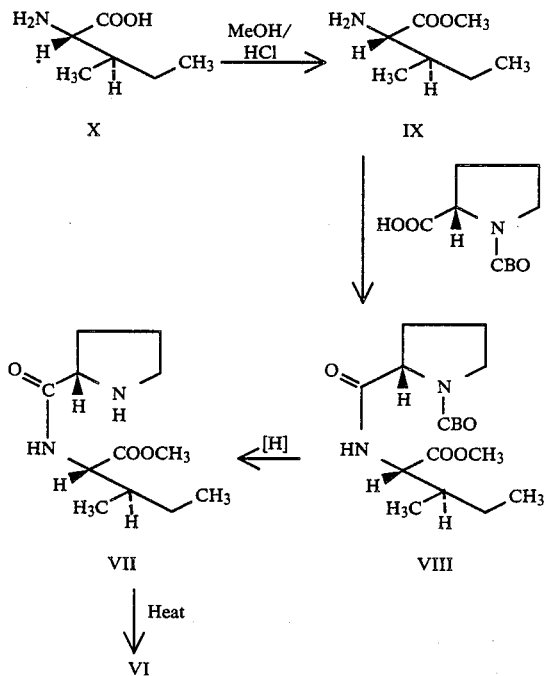

The compounds of formula IX, VIII, VII, VI, IV and II per se form part of the present invention.

The aminocyclols are preferably produced in optically pure form from optically active compounds as described above. If desired some of the starting materials may be in racemic form and on reaction with an optically active starting material, the diastereoisomers may be separated in conventional manner, e.g. chromatography. For example the compound of formula VI may be separated from its epimers, e.g. produced from a mixture of isoleucine including the compound of formula X and diastereoisomers and epimers thereof obtainable from glycine.

The so-obtained compounds of the invention and their acid addition salts thereof may be isolated according to known methods and purified e.g. by high performance liquid chromatography, other chromatographic techniques or crystallisation.

The present invention in another aspect provides a compound of the invention in the presence of less than 5%, less than 2%, or less than 1%, of the corresponding 5'S-(2S-butyl) epimer, e.g. dihydro-β-ergocryptine or an acid addition salt thereof.

The presence of an epimer may be detected by conventional analytical techniques, e.g. high performance liquid chromatography or nuclear magnetic resonance.

A compound of the invention or an acid addition salt thereof wherein $R_1$ is isopropyl (hereinafter 5'S-(2R-butyl)), and dihydro-β-ergocryptine (hereinafter 5'S-(2S-butyl)) may be distinguished according to n.m.r. peak shifts, according to the $^1$H NMR spectrum (360 MHz; solvent CDCl$_3$; standard tetramethylsilane) as follows:

| (ppm)    | 5'S—(2R—butyl) | 5'S—(2S—butyl) |
|----------|----------------|----------------|
| C-5'-H   | 4.53           | 4.50           |
| C-13'-H  | 1.30           | 1.50           |

According to the $^{13}$C NMR spectrum (360 Mhz; 30 mg/1.5 ml; pD=3.4) the compounds may be distinguished as follows:

| (ppm)          | 5'S—(2R—butyl) | 5'S—(2S—butyl) |
|----------------|----------------|----------------|
| CH$_3$ on C-13' | 17.5           | 16.4           |
| CH$_2$ on C-13' | 27.4           | 28.6           |

Thus the presence of 1% or more of the 5'S-(2S-butyl) epimers in the compounds of the invention may be detected.

A suitable system for high performance liquid chromatography comprises a solvent system of (a) 1% triethylamine in water mixed with (b) 1% triethylamine in acetonitrile. The solvent system initially comprises 15% (b) and this is increased to 50% (b) over 20 minutes. The system is caused to flow at 2 ml/minute through a column RP 18 (Knauer) length 25 cm diameter 4.6 mm. The 5'S-(2R-butyl) compound of example 1 had a retention time of 19 minutes. Beta-dihydroergocryptine had a retention time of 20 minutes.

Another suitable solvent system is water/acetonitrile/tetramethylammonium chloride/trimethylamine (755 g:240 g:4 g:1 g); solid phase LiChromosorb (Merck) R 18 (particle diameter 10 um; column diameter 16 mm; length 25 cm).

Insofar as the production of any starting matrial, e.g. for compounds of the invention other than those of formula I, is not particularly described, then they may be produced and purified in analogous manner to that described herein in respect of those for the compounds of formula I or in conventional manner for analogous compounds.

In the following examples all temperatures are in degrees Centigrade and are uncorrected.

High vacuum refers to ca 0.01 mm mercury.

All optical rotations are at 20° C. and at the sodium D line except where otherwise states.

All N.M.R. shifts (delta) refer to ppm; m=multiplet; s=singlet; q=quartet; t=triplet.

EXAMPLE 1

(5R,8R,10R)-N-[(2R,5S,11S,12S)-5-(2R-butyl)octahydro-12-hydroxy-2-isopropyl-3,6-dioxo-8H-oxazolo[3,2-a]pyrrolo[2,1-c]pyrazin-yl]-6-methylergoline-8-carboxylic acid amide also identified as (5'α,10α)-9,10-dihydro-12'-hydroxy-2'-(1-methylethyl)-5'-[(R)-1-methylpropyl]ergotaman-3',6',18-trione according to Chemical abstracts 9th Collective Index nomenclature 1.8 ml (22.5 mM) trifluoroacetic acid is added to a mixture of 5.36 g (20 ml) anhydrous 9,10-dihydrolysergic acid (5R,8R,10R), 40 ml absolute dimethylformamide and 20 ml absolute acetonitrile. 2.8 ml trifluoroacetic acid anhydride (20 ml) and 20 ml pyridine are added at −10°. The reaction mixture is stirred further for 5 minutes at −10° and then 3.62 g (10 mM) (2R,5S,11S,12S)-2-amino-5-(2R-butyl)-octahydro-12-hydroxy-2-isopropyl-3,6-dioxo-8H-oxazolo[3,2-a]pyrrolo[2,1-c]pyrazine monohydrochloride is added. The reaction mixture is stirred and allowed to warm to 22° during 2 hours. The mixture is partitioned between methylene chloride and water. The organic phase is dried with sodium sulphate, filtered and concentrated. The residue is crystallised from ethyl acetate/ether.

M.pt. 190°–191°; $[\alpha]^{20} = -43.5°$ (c=0.5 in pyridine).

NMR 360 MHz (CDCl$_3$) 0.98 ppm (6H, t), 1.08–1.17 (6H, q), 1.3 (1H, m, C-13-H), $^{13}$C-NMR 360 MHz (30 mg/1.5 ml, pD=3.4): No visible signal at 16.4 or 28.6 ppm that can be attributed to the epimer, dihydro-β-ergocryptine, indicating that less than 1% of the epimer is present.

The starting material (2R,5S,11S,12S)-2-amino-5-(2R-butyl)octahydro-12-hydroxy-2-isopropyl-3,6-dioxo-8H-oxazolo[3,2-a]pyrrolo[2,1-c]pyrazine monohydrochloride is produced as follows:

(a)
(3S,8aS)-3-(2R-butyl)-hexahydro-pyrrolo[1,2-a]piperazine-1,4-dione (compound of formula VI)

(i) (2S,3R)-L-allo-isoleucine methyl ester 30 g (229 mM) (2S,3R)-L-Allo-isoleucine ($[\alpha]^{20} = +45 \pm 2°$; [c=5 in 6M HCl]) is dissolved in 300 ml 6.8N methanolic hydrochloric acid and stirred at room temperature for 18 hours. The mixture is concentrated and the residue shaken with 300 ml saturated potassium carbonate solution and 600 ml ether. The aqueous phase is then extracted three times each with 600 ml ether. The combined organic phases are dried over sodium sulphate, filtered, concentrated and dried to a constant weight in a high vacuum to give a clear light yellow oil of the (2S,3R)-L-allo-isoleucine methyl ester. Further methyl ester is obtained by extracting the above mentioned aqueous phase.

$[\alpha]^{20} = 45°$ (c=3 in CH$_2$Cl$_2$); NMR 100 MHz (CDCl$_3$) 0.81–1.01 ppm (6H, 4 Peaks, CH$_3$-C-3, CH$_3$-CH$_2$-C-3), 3.46 (1H, d, J=4 Hz, C-2-H), 3.71 (3H, s, COOCH$_3$).

(ii) Condensation with CBO-L-Proline 26.15 g (161.5 mM) solid N,N-carbonyldiimidazolyl is added with stirring to 40.35 g (161.5 mM) 2S-carbobenzoxy-L-proline in 600 ml tetrahydrofuran. After 5 minutes the CO$_2$ evolution finished. The mixture is light yellow and is stirred for a further 1 hour at room temperature. To this mixture a solution of 22.95 g (158.3 mM) (2S,3R)-L-allo-isoleucine methyl ester in 155 ml tetrahydrofuran is added dropwise.

The mixture is stirred for 2 hours at room temperature, shaken and extracted with 1 liter ether. The organic phase is washed twice with water. The aqueous washings are re-extracted with ether.

The combined organic phases are dried over sodium sulphate, filtered, concentrated and dried in a high vacuum at 30° to give a compound of formula VIII as a clear light yellow oil.

(iii) Removal of the CBO group

A solution of 64 g (170 mM) of the compound of formula VIII in 800 ml ethanol is added as a prehydrogenated mixture of 12 g 10% palladium-on-charcoal catalyst in 500 ml methanol. The mixture is hydrogenated (room temperature, 757 mm Hg, reaction time 2½ hours) taking up 2.9 liters hydrogen. The reaction mixture is filtered through a filtering aid such as Hyflo, washed with 1 liter CH$_2$Cl$_2$/CH$_3$OH (1:1) and dried to give after concentration a compound of formula VII as a yellow oil.

(vi) Cyclization to diketo piperazine (compound of formula VI)

The compound of formula VII is heated in a high vacuum at 120° for 2½ hours. The resultant partially crystalline mixture is stirred with ether.

Hexane is added forming a crystalline component (8.66 g) and an oily component (27.4 g). The oily component was then re-subjected to the cyclization reaction.

The crystalline component which is the heading compound is recrystallized from ether/hexane to give colourless needles. M.pt. 132°–135°; $[\alpha]^{20} = -156°$ (c=1 in CH$_2$Cl$_2$).

NMR 360 MHz (CDCl$_3$) 0.80 ppm (3H, d, J=6,5 Hz, CH$_3$-C-9), 0.98 (3H, t, J=7 Hz, CH$_3$-CH$_2$-C-9), 1.42 (2H, m), 1.92 (1H, m), 2.45 (2H, m), 2.38 (2H, m), 3.52 bis 3.59 (2H, m), 4.08 (2H, m).

(b)
(2R,5S,11S,12S)-5-(2R-butyl)-octahydro-12-hydroxy-2-isopropyl-3,6-dioxo-8H-oxazolo[3,2-a]pyrrolo[2,1-c]pyrazine-2-carboxylic acid ethyl ester [compound of formula IV]

(i) 21 g (100 mM) (3S,8aS)-3-(2R-butyl)-hexahydro-pyrrolo[1,2-a]piperazine-1,4-dione are mixed with 200 ml absolute dioxane, 57.3 ml (334 mM) N-ethyl-N,N-diisopropylamine and 53.32 g (178.6 mM) S-(+)-2-benzyloxy-2-chloroformyl-3-methyl-butyric acid ethyl ester under nitrogen and boiled under reflux for 3 hours. The reaction mixture is cooled and partitioned between 1 liter ether and cold 1N hydrochloric acid. The organic phase is twice washed with saturated potassium bicarbonate solution and the aqueous phase reextracted with ether. The combined organic phases are dried over sodium sulphate, filtered and concentrated to give a yellow oil of the condensed product.

(ii) This product is treated with a prehydrogenated mixture of 10 g 10% palladium on charcoal catalyst in 2.6 liters absolute ethanol. The mixture is hydrogenated for 18 hours at normal pressure, filtered through a filtering aid such as Hyflo, and evaporated. The residue is dried in a high vacuum to give a yellow oil which is recrystallised from ether/petroleum ether to give the heading compound.

M.pt. 95°–96°; $[\alpha]^{20} = +9°$ (c=1 in ethanol).

(c)
(2R,5S,11S,12S)-5-(2R-butyl)-octahydro-12-hydroxy-2-isopropyl-3,6-dioxo-8H-oxazolo[3,2-a]pyrrolo[2,1-c]pyrazine-2-carboxylic acid 172 ml 1N sodium hydroxide are added to 28.64 g of the ester obtained in step (b) suspended in 20 ml methanol. The resultant colourless solution is stirred for 19 hours at room temperature, and then washed twice with 500 ml ether. The combined organic washings are back-extracted with water. All the aqueous phases are made acid with 103.2 ml 2N hydrochloric acid at 0° and the heading compound falls out of solution as an oil. A crystallizate is obtained after treatment in an ultrasound bath, and is then dried at 50° for 24 hours. The heading compound is in the form of colourless crystals. M.pt. 114°–115°; second crystalline form: M.pt. 172°–173°; $[\alpha]^{20} = -11.7°$ (c=1.5 in pyridine).

(d)
(2R,5S,11S,12S)-5-(2R-butyl)-octahydro-12-hydroxy-2-isopropyl-3,6-dioxo-8H-oxazolo[3,2-a]pyrrolo[2,1-]pyrazine-2-carboxylic acid azide A solution of 8.37 ml oxalyl chloride in 33 ml methylene chloride is added to a solution of 9.04 ml dimethylformamide in 132 ml methylene chloride at −10° to form a white suspension which is stirred for a further 15 minutes at −10°.

23.36 g (65.8 mM) of the acid obtained in step (c) in solid form are added and the temperature of the mixture rises to −6°. The resultant bright yellow solution is stirred for a further 30 minutes at −60°. A solution of 42.9 g sodium azide in 204 ml water is added over 4 minutes. The temperature of the mixture rises to +5° and the mixture becomes reddish. The mixture is stirred for a further 15 minutes at −10°, and extracted with 900 ml methylene chloride. The organic phases are shaken with 420 ml of an ice-cold saturated potassium bicarbonate solution. The aqueous phase is twice back-extracted with 800 ml methylene chloride. The combined organic phases are dried over sodium sulphate, filtered, concentrated and dried in a high vacuum. The residue is recrystallized from ether/methylene chloride to give colourless crystals.

M.pt. greater than 175° (decomposition).

(e)
(2R,5S,11S,12S)-5-(2R-butyl)-octahydro-12-hydroxy-2-isopropyl-3,6-dioxo-8H-oxazolo[3,2-a]pyrrolo[2,1-c]-pyrazine-2-carbaminic acid benzyl ester 13.52 ml (130.8 mM) absolute benzyl alcohol is added to a solution of 16.54 g (43.6 mM) in 110 ml of the acid azide obtained in step (d) and boiled under reflux for 35 minutes. The easily vaporized part of the resultant clear yellow solution is distilled off and the surplus benzyl alcohol taken off at 120° in a high vacuum. The resultant crystalline yellow residue is purified by stirring in ether and crystallization from methylene chloride/ether.

M.pt. 197°–199°; $[\alpha]^{20} = +40°$ (c=0.6 in methanol).

(f)
(2R,5S,11S,12S)-2-amino-5-(2R-butyl)-octahydro-12-hydroxy-2-isopropyl-3,6-dioxo-8H-oxazolo[3,2-a]pyrrolo[2,1-c]pyrazinemonohydrochloride
(compound of formula II)

16 g (34.8 mM) of the carbaminic acid derivative obtained in step (e), 8 g of 10% palladium-on-charcoal catalyst, 1.12 liters methanol and 112 mM hydrochloric acid are mixed and hydrogenated at 19° under normal pressure. The mixture is filtered. The filtrate is concentrated at 30° until it begins to crystallize, mixed with 500 ml ether and stirred. The crystallizate is filtered off, washed with ether and dried to a constant weight under a high vacuum. M.pt. greater than 145° (decomp.). $[\alpha]^{20} = +55°$ (c=0.15 in dimethylformamide).

The compounds of the invention and their pharmaceutically acceptable acid addition salts thereof, hereinafter referred to as the pharmaceutical compounds of the invention, are new and exhibit pharmacological activity and are therefore useful as pharmaceuticals.

In particular the pharmaceutical compounds of the invention exhibit a prolactin secretion inhibition activity as indicated in standard animal tests. For example, in one test according to the method of E. Flückiger et al., Experienta 34, 1330–1332, 1978, the administration subcutaneously of the pharmaceutical compounds of the invention at a dose of from about 0.1 mg/kg to about 10 mg/kg animal body weight inhibit implantation in the rat.

In this test the title compound of example 1 has a ED$_{50}$ of about 1.84 mg/kg s.c.. The compound is thus some 5 times more active than co-dergocrine in this test.

The pharmaceutical compounds of the invention are therefore useful for use as prolactin secretion inhibitors, e.g. for the treatment of lactation, galactorrhaea, hyperprolactinaemic hypogonadism, acromegaly, or prolactinoma.

The pharmaceutical compounds of the invention also exhibit serotoninergic activity as indicated in standard animal tests. For example, in the sleep/wake cycle test at dministration i.p. at from about 0.3 to about 10 mg/kg or p.o. at from about 1 to about 10 mg/kg animal body weight the compounds induce a reduction of the paradoxical sleep phase and a prolongation of the wake phase, in accordance with the principles described in J. M. Vigouret et al., Pharmacology, 16, (Suppl. 1), 1,156-173 (1978).

The serotoninergic activity is confirmed in that the comounds inhibit the reserpine syndrome in the PGO-potential model in implanted cats on administration of from about 0.01 to about 1 mg/kg i.v. in accordance with the above mentioned article of J. M. Vigouret et al.

In this test the example 1 compound had an ID$_{50}$ of 0.11 mg/kg i.v. and is thus indicated to be 3 times more active than co-dergocrine in this test.

Moreover the compounds increase the local cerebral glucose utilisation in the sensomotor cortex, e.g. Hippocampus and Nucleus habenula, as indicated by the carbon-14-2-deoxyglucose autoradiographic technique with the rat brain on administration i.p. of from about 0.01 to about 3 mg/kg of the compounds [for method see e.g. L. Solokoff, Journal of Cerebral Blood Flow and Metabolism, 1981, (1), 7–36; H. E. Savaki et al., Brain Research 1982, 233, 347–358, and J. McCulloch et al., Journal of Cerebral Blood Flow and Metabolism 1981, 1, 133–136].

The pharmaceutical compounds of the invention are thus additionally useful for use in the treatment of cerebral insufficiency, e.g. for senile dementia, particularly the early forms thereof, and for increasing vigilance.

Furthermore, the pharmaceutical compounds of the invention exhibit sympatholytic α-blocking activity as indicated in standard tests. For example, in the infusion cat this activity can be shown on administration i.v. of doses from about 0.01 to about 1 mg/kg s.c.. An anti-hypertensive effect is seen in the anaesthetized normotonic dog on administration i.v. from about 0.001 mg/kg to about 10 mg/kg animal body weight in accordance with the method of D. Chu., A. Hofma nn and E. Stürmer, Naunyn-Schmiedeberg's Arch. Pharmacol. (1975), Suppl. 287, R 18, and in the spontaneously hypertensive rat in administration of from 0.01 mg/kg s.c. to 10 mg/kg i.c..

In general the compound of Example 1 is on average of 1 to 3 times more potent than co-dergocrine in this test.

The compounds are therefore furtheremore useful as anti-h hypertensives, especially for geriatrics.

The pharmaceutical compounds of the invention increase the cerebrovascular blood flow, as indicated in standard tests. For example the compounds increase the post-ischemic FEG recovery in the isolated rat head test on administration of from about 0.2 to about 0.4 ug/min into the carotid artery according to the method of N. Wiernsperger, P. Gygax, O. Hünziker and A. Schweizer, J. Pharmacol. (Paris), 1979, 10, 4 bis p. 489 to 5G1 at 495, and P. Gygax and N. Wiernsperger Proc. Int. Cerebrovascular diseases, SIR (1980), p. 234–254.

The pharmaceutical compounds of the invention are therefore useful—in the treatment of stroke.

The compounds of the invention and their pharmaceutically acceptable acid addition salts are therefore indicated for use as pharmaceuticals, for use as a prolactin secretion inhibitor, for increasing vigilance, for the treatment of senile dementia, hypertension or stroke. The senile dementia or anti-hypertension indication is the preferred indication. The title compound of Example 1 is the preferred compound.

For all these uses the dosage will, of course, vary depending on the compound employed, mode of administration and treatment desired. However, in general, satisfactory results are obtained when administered at a daily dosage of from about 0.001 mg to about 10 mg per kg animal body weight, conveniently given in divided doses 2 to 4 times a day or in sustained release form. For the larger mammals, the total daily dosage is in the range from about 0.3 to about 30 mg, and dosage forms suitable for e.g. oral administration comprise from about 0.1 mg to about 15 mg of the compounds admixed with a solid or liquid pharmaceutical carrier or diluent.

For the title compound of example 1 the preferred oral daily dosage is from 2 to 4 mg.

The exact dosage of the pharmaceutical compounds of the invention will depend on a number of factors, including their activity in the above tests relative to standard compounds, e.g. co-dergocrine, also identified as ergoloid mesylates, which is used for senile dementia and hypertension. As indicated by the results given above, the title compound of Example 1 is more active than co-dergocrine in the tests mentioned. It is thus indicated that the title compound of Example 1 would be administered at the same or lower dosages than co-dergocrine.

In general pharmaceutical compositions of the invention in unit dosage form contain at least 0.01 mg or at least 0.1 mg of a compound of the invention or a pharmaceutically acceptable acid addition salt thereof and at least 0.1% by weight, e.g. up to 90% by weight, e.g. from 1 to 10% by weight, of a compound of the invention or a pharmaceutically acceptable acid addition salt thereof.

Particularly suitable unit dosage forms for e.g. oral or rectal administration contain from about 0.1 to 15 mg, or especially from 0.1 to 9 mg, of a compound of the invention or a pharmaceutically acceptable acid addition salt thereof. The unit dosage forms may be in the form of for example tablets, capsules, dragees or suppositories.

Liquid solutions, e.g. drop solutions for oral use may contain at least 0.1 mg/per ml, e.g. 0.5 mg to 2 mg, per ml.

Particularly suitable unit dosage forms e.g. for parenteral administration, e.g. a sterile injectable suspension, contain from about 0.01 to about 3 mg, or especially from 0.03 to 1 mg of a compound of the invention or a pharmaceutically acceptable acid addition salt thereof.

The compounds of the invention may if desired be administered in the pharmaceutically acceptable acid addition salt thereof. Such salts exhibit the same order of activity as the compound of the invention as such in feed base form. It is preferred to administer the compound of the invention in the free base form.

The present invention accordingly provides a pharmaceutical composition comprising a compound of the invention or a pharmaceutically acceptable acid addition salt thereof in association with a pharmaceutical carrier or diluent. Such formulations may be made in conventional manner, e.g. as known for other ergot peptide alkaloids, e.g. co-dergocrine.

Thus the compounds of the invention and their pharmaceutically acceptable acid addition salts may be mixed with pharmaceutically acceptable carriers and diluents and if desired other excipients to produce pharmaceutical compositions for oral, rectal or parenteral administration. Thus tablets, granulates, dispersable powders, dragees, capsules, syrups, suspensions, solutions and elixirs may be produced for oral administration. Suppositories for rectal administration and solutions and suspensions for parenteral administration may also be produced. Oral pharmaceutical compositions may include one or more excipients, e.g. sweetening agents, aroma, dyestuffs, and conserving agents in order to produce an acceptable and palatable composition.

For example, tablets may contain a compound of the invention or a pharmaceutically acceptable acid addition salt thereof admixed with diluents, e.g. calcium carbonate or lactose, dispersing agents, such as starch and alginic acid, binding agents such as starch, polyvinylpyrrolidone or gelatine, lubricating agents such as magnesium stearate, stearic acid or talc. The tablets may be coated using conventional techniques in order to delay the disintegration thereof and retard the resorption in the gastro-intestinal tract in order to produce prolonged activity.

Capsules may contain an ergot 5S-(2R-butyl) peptide alkaloid or a pharmaceutically acceptable acid addition salt thereof admixed with a solid diluent such as lactose or starch and a lubricant, e.g. magnesium stearate.

Suspensions, sirups and elixirs may contain an ergot 5'S-(2R-butyl) peptide alkaloid admixed with conventional excipients for such compositions such as suspending agents, e.g. methyl cellulose, tragacanth and sodium alginate, tensioactive agents such as lecithin, polyoxyethylene stearate or polyoxyethylene sorbitan monooleate and conversing agents such as ethyl para-hydroxy benzoate.

Injectable compositions, suppositories and other pharmaceutical compositions may indicated as above be produced in conventional manner.

From the point of view of ease of production and acceptability solid dosage forms are preferred, e.g. tablets or capsules.

Examples of pharmaceutical compositions, which may be produced in conventional manner, are as follows:

| Tablets | Weight |
|---|---|
| Constituent | |
| Compound of the invention, e.g. title compound of Example 1 | 0.1 mg |
| Tartaric acid | 0.1 mg |
| Lactose | 85.9 mg |
| Corn starch | 10 mg |
| Gelatine | 0.3 mg |
| Magnesium stearate | 0.3 mg |
| Talc | 2 mg |
| Capsules | |
| Compound of the invention, e.g. title compound of Example 1 | 0.1 mg |
| Diluents and lubricants (lactose, starch, magnesium stearate) | 299.9 mg |

| | WEIGHT (mg) | |
|---|---|---|
| Liquid compositions | Sterile injectable suspension | Oral liquid suspension |
| Compound of the invention, e.g. title compound of Example 1 | 0.05 | 0.1 |
| Sodium carboxymethyl cellulose USP | 1.25 | 12.5 |
| Methylcellulose | 0.4 | — |
| Polyvinylpyrrolidone | 5 | — |
| Lecithin | 3 | — |
| Benzyl alcohol | 0.01 | — |
| Magnesium aluminium silicate | — | 47.5 |
| Aroma | — | q.s. |
| Dyestuff | — | q.s. |
| Methylparaben, USP | — | 4.5 |
| Propylparaben, USP | — | 1.0 |
| Polysorbate 80 (e.g. Tween 80), USP | — | 5 |
| Sorbitol solution, 70%, USP | — | 2,500 |
| Stabilizing buffer | q.s. | q.s. |
| Water | q.s. to 1 ml | q.s. to 5 ml |

The above composition may be administered, e.g. once daily, for the treatment of senile dementia.

The compounds of the invention or their pharmaceutical acceptable acid addition salts may be administered from about 1 to 30 mg/kg animal body weight daily over 4 weeks to dogs and show a good general tolerability. For example, the title compound of example 1 shows very slight ergot specific side effects up to 10 mg/kg animal body weight p.o. over 4 weeks, e.g. only slight emesis, salivation, loss of weight, and reduction in feed uptake.

At 30 mg/kg animal body weight p.o. no significant cardiotoxic effects are observed. Thus the title compound of Example 1 is indicated to be well tolerated, even better than co-dergocrine.

I claim:

1. A compound of formula I

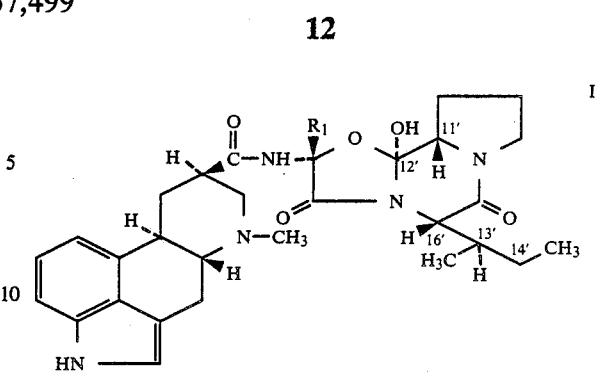

wherein $R_1$ is methyl, ethyl or isopropyl, or an acid addition salt thereof.

2. A compound of claim 1 which is (5R,8R,10R)-N-[(2R,5S,11S,12S)-5-(2R-butyl)-octahydro-12-hydroxy-2-isopropyl-3,6-dioxo-8H-oxazolo[3, 2-a]pyrrolo[2,]-c]pyrazinyl]-6-methyl-ergoline-8-carboxylic acid amide or an acid addition salt thereof.

3. A pharmaceutical composition for treating sensile dementia comprising a compound as claimed in claim 1 or a pharmaceutically acceptable acid addition salt thereof in association with a pharmaceutical carrier or diluent.

4. A pharmaceutical composition as claimed in claim 3 in unit dosage form containing at least 0.01 mg of the compound or a pharmaceutically acceptable acid addition salt thereof.

5. A pharmaceutical composition as claimed in claim 3 containing from 0.1 to 15 mg of the compound or a pharmaceutically acceptable acid addition salt thereof.

6. A pharmaceutically composition as claimed in claim 5 for oral or rectal use containing from 0.1 to 9 mg of the compound or a pharmaceutically acceptable acid addition salt thereof.

7. A pharmaceutically composition as claimed in claim 4 containing from 0.01 to 3 mg of the compound or a pharmaceutically acceptable acid addition salt thereof.

8. A pharmaceutically composition as claimed in claim 4 for parenteral use containing from 0.01 to 1 mg of the compound or a pharmaceutically acid addition salt thereof.

9. A pharmaceutical composition for treating senile dementia in solution form containing at least 0.1 mg per ml of a compound as claimed in claim 1 or a pharmaceutically acceptable acid addition salt thereof.

10. A method of treating senile dementia in a subject which comprises administering a therapeutically effective amount of a compound of claim 1 to a subject in need of such treatment.

11. A compound of formula I

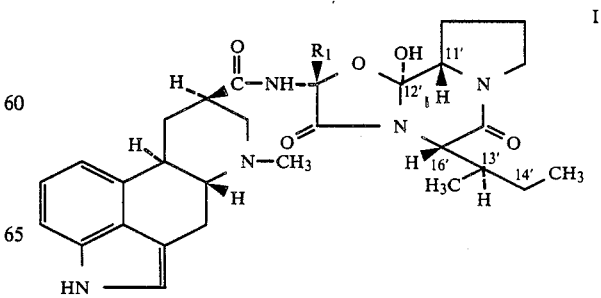

wherein R₁ is methyl, ethyl or isopropyl, or an acid addition salt thereof in admixture with less than 5% by weight of the corresponding 5'S-(2S-butyl) epimer.

12. A compound of claim 11 or an acid addition salt thereof, in admixture with less than 1% by weight of the corresponding 5'S-(2S-butyl) epimer.

13. A compound of claim 11 which is (5R,8R,10R)--N-[(2R,5S,11S,12S)-5-(2R-butyl)-octahydro-12-hydroxy-2-isopropyl-3,6-dioxo-8H-oxazolo[3,2-a]pyrrolo[2,1-c]pyrazinyl]-6-methyl-ergoline-8-carboxylic acid amide or an acid addition salt thereof.

14. A compound of claim 13 or an acid addition salt thereof in admixture with less than 1% by weight of dihydro-β-ergocryptine or an acid addition salt thereof.

15. A pharmaceutical composition for treating senile dementia comprising a therapeutically effective amount of a compound as claimed in claim 11 or a pharmaceutically acceptable acid addition salt thereof in association with a pharmaceutical carrier or diluent.

16. A pharmaceutical composition as claimed in claim 15 in unit dosage form containing at least 0.01 mg of the compound or a pharmaceutically acceptable acid addition salt thereof.

17. A pharmaceutical composition as claimed in claim 15 containing from 0.1 to 15 mg of the compound or a pharmaceutically acceptable acid addition salt thereof.

18. A pharmaceutical composition as claimed in claim 17 for oral or rectal use containing from 0.1 to 9 mg of the compound or a pharmaceutically acceptable acid addition salt thereof.

19. A pharmaceutical composition as claimed in claim 16 containing from 0.01 to 3 mg of the compound or a pharmaceutically acceptable acid addition salt thereof.

20. A pharmaceutical composition as claimed in claim 16 for parenteral use containing from 0.01 to 1 mg of the compound or a pharmaceutically acceptable acid addition salt thereof.

21. A pharmaceutical composition for treating senile dementia in solution form containing at least 0.1 mg per ml of a compound as claimed in claim 11 or a pharmaceutically acceptable acid addition salt thereof.

22. A pharmaceutical composition for oral use containing from 0.1 to 15 mg of the compound of claim 2 or a pharmaceutically acceptable acid addition salt thereof.

23. A pharmaceutical composition for oral use containing from 0.1 to 9 mg of the compound of claim 2 or a pharmaceutically acceptable acid addition salt thereof.

24. A pharmaceutical composition for parenteral use containing from 0.03 to 1 mg of the compound of claim 2 or a pharmaceutically acceptable acid addition salt thereof.

25. A pharmaceutical composition in solution form containing at least 0.5 to 2 mg per ml of a compound of claim 2 or a pharmaceutically acceptable acid addition salt thereof.

* * * * *